United States Patent [19]

Cartmell et al.

[11] Patent Number: 4,827,939
[45] Date of Patent: May 9, 1989

[54] MEDICAL ELECTRODE WITH REUSABLE CONDUCTOR AND METHOD OF MANUFACTURE

[75] Inventors: James V. Cartmell; Larry R. Burcham, both of Dayton; Michael L. Wolf, West Milton, all of Ohio

[73] Assignee: Baxter International Inc., Deerfield, Ill.

[21] Appl. No.: 170,129

[22] Filed: Mar. 14, 1988

Related U.S. Application Data

[60] Continuation of Ser. No. 920,028, Oct. 16, 1986, abandoned, Division of Ser. No. 956,752, Jul. 18, 1985, Pat. No. 4,635,642.

[51] Int. Cl.$^4$ .............................................. A61B 5/04
[52] U.S. Cl. .................................... 128/640; 128/798
[58] Field of Search ............... 128/639, 640, 641, 783, 128/798; 439/680, 681, 441

[56] References Cited

U.S. PATENT DOCUMENTS

| | | | |
|---|---|---|---|
| 2,563,760 | 8/1945 | Uline | 339/258 R |
| 2,968,780 | 1/1961 | Roswell | 339/95 D |
| 3,296,577 | 10/1964 | Travis et al. | 339/258 R |
| 3,357,930 | 12/1967 | Marks et al. | 252/408.1 |
| 3,362,633 | 1/1967 | Allison et al. | 128/641 |
| 3,518,984 | 10/1967 | Mason | 128/640 |
| 3,805,769 | 4/1974 | Sessions | 128/641 |
| 3,868,946 | 3/1975 | Hurley | 128/641 |
| 3,946,730 | 3/1976 | Monter | 128/641 |
| 3,976,055 | 8/1976 | Monter et al. | 128/641 |
| 3,993,049 | 11/1976 | Kater | 128/640 |
| 3,998,215 | 12/1976 | Anderson et al. | 128/641 |
| 4,051,842 | 10/1977 | Hazel et al. | 128/640 |
| 4,066,078 | 1/1978 | Berg | 128/641 |
| 4,067,322 | 1/1978 | Johnson | 128/641 |
| 4,090,752 | 5/1978 | Long | 312/42 |
| 4,125,110 | 11/1978 | Hymes | 128/641 |
| 4,141,366 | 2/1979 | Cross Jr. et al. | 128/640 |
| 4,257,424 | 3/1981 | Cartmell | 128/641 |
| 4,274,420 | 6/1981 | Hymes | 128/641 |
| 4,319,579 | 3/1982 | Cartmell | 128/640 |
| 4,329,999 | 5/1982 | Phillips | 156/247 |
| 4,331,153 | 5/1982 | Healy | 128/641 |
| 4,353,373 | 10/1982 | Sessions et al. | 128/641 |
| 4,370,984 | 2/1983 | Cartmell | 128/641 |
| 4,403,824 | 9/1983 | Scott | 339/186 R |
| 4,409,981 | 10/1983 | Lundberg | 128/640 |
| 4,441,500 | 4/1984 | Sessions et al. | 128/641 |
| 4,488,557 | 12/1984 | Engel | 128/640 |
| 4,490,005 | 12/1984 | Hovey | 128/641 |
| 4,493,525 | 1/1985 | Hall et al. | 339/176 MP |
| 4,522,211 | 6/1985 | Bare et al. | 128/640 |
| 4,524,087 | 6/1985 | Engel | 128/640 |
| 4,617,935 | 10/1986 | Cartmell et al. | 128/641 |
| 4,622,089 | 11/1986 | Lauritzen | 156/289 |

FOREIGN PATENT DOCUMENTS

| | | |
|---|---|---|
| 0070626 | 6/1982 | European Pat. Off. . |
| 8500017 | 1/1985 | European Pat. Off. ............ 128/802 |
| 0142372 | 5/1985 | European Pat. Off. . |
| 2724461 | 12/1977 | Fed. Rep. of Germany . |
| 3136193 | 4/1983 | Fed. Rep. of Germany . |
| 8101646 | 6/1981 | PCT Int'l Appl. . |

*Primary Examiner*—Edward M. Coven
*Assistant Examiner*—Randy Citrin
*Attorney, Agent, or Firm*—Roger S. Dybvig

[57] ABSTRACT

A medical electrode intended for short term use has a disposable electrode pad provided with a socket and a reusable electrode conductor which is attached to a lead wire and which has a ridged body adapted to enter and be retained by the socket. The pad includes a pair of spaced foam sheets with patient-contacting adhesive layers on their lower surfaces. An electrolyte gel matrix, preferably formed from conductive adhesive urethane hydrogel, is located between the foam sheets. The socket is formed in a relatively stiff socket plate that overlies the gel matrix and the foam sheets. The socket includes a bore located over the gel matrix shaped to receive the electrode conductor, which is slightly larger than the bore, and may optionally include outwardly extending slits projecting from the bore. A method of manufacturing a strip of the electrode pads on a release liner on a continuous basis is disclosed. In a modification for longer term monitoring uses, the electrode pads are constructed to confine the gel matrix to avoid gel dry out and the socket and the conductor are provided with a cooperating key and keyway for restraining relative movements therebetween.

34 Claims, 2 Drawing Sheets

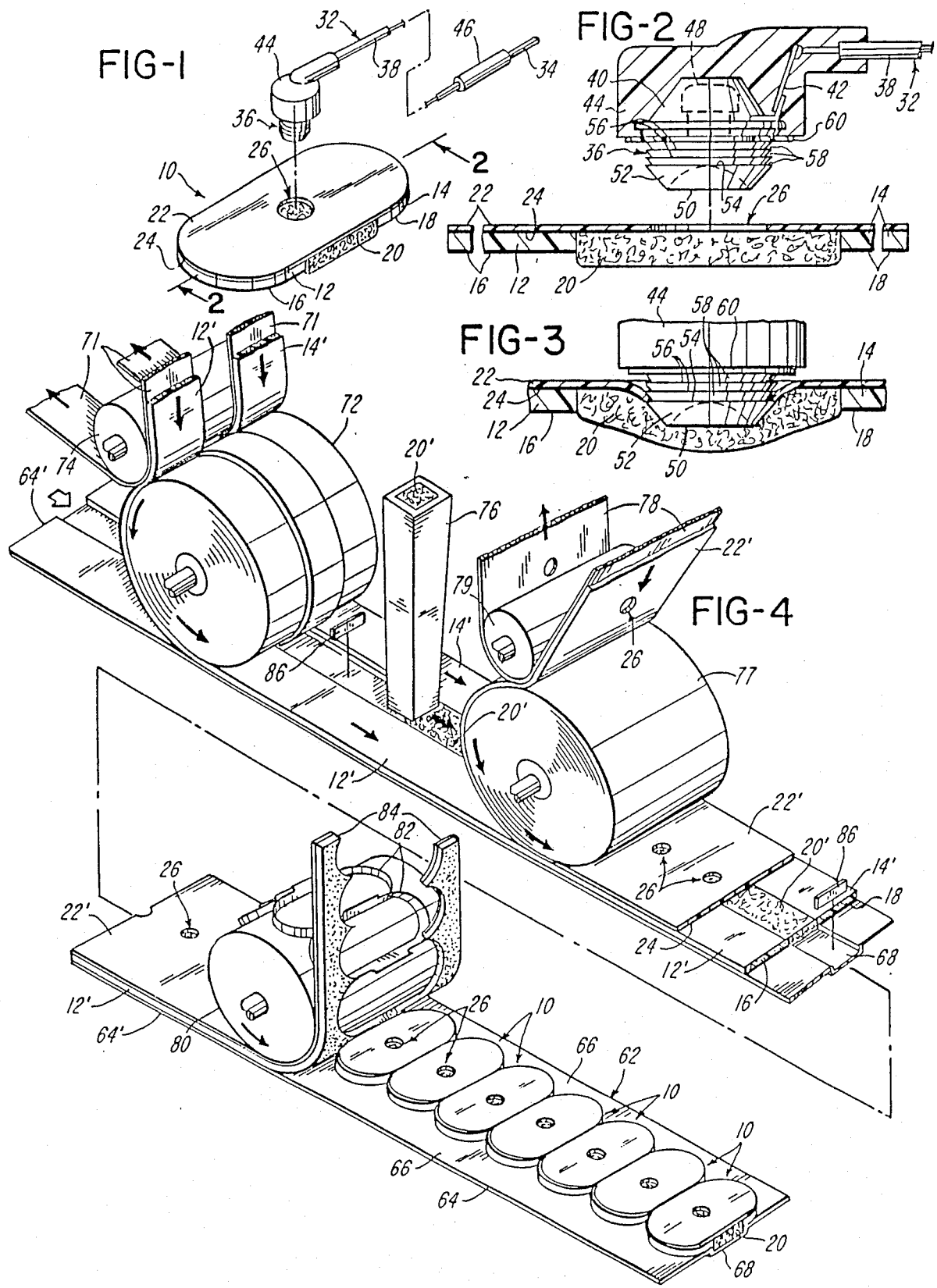

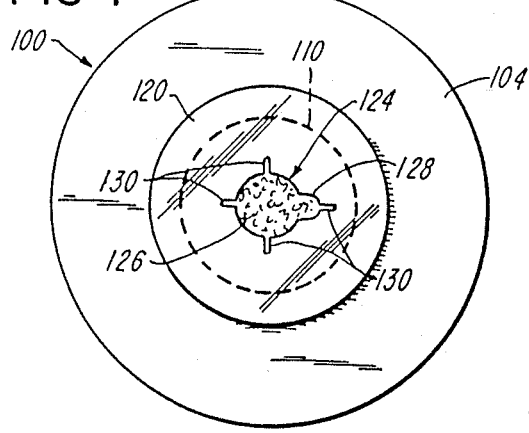
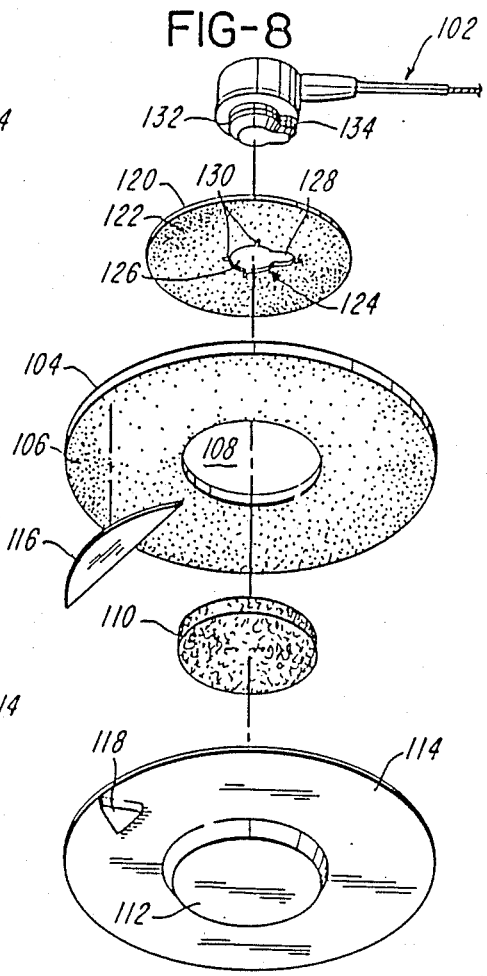
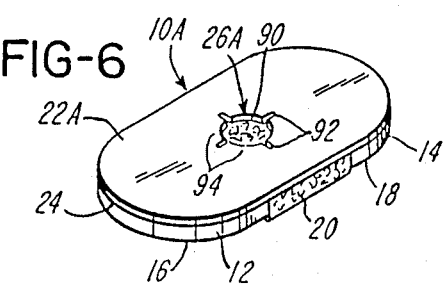
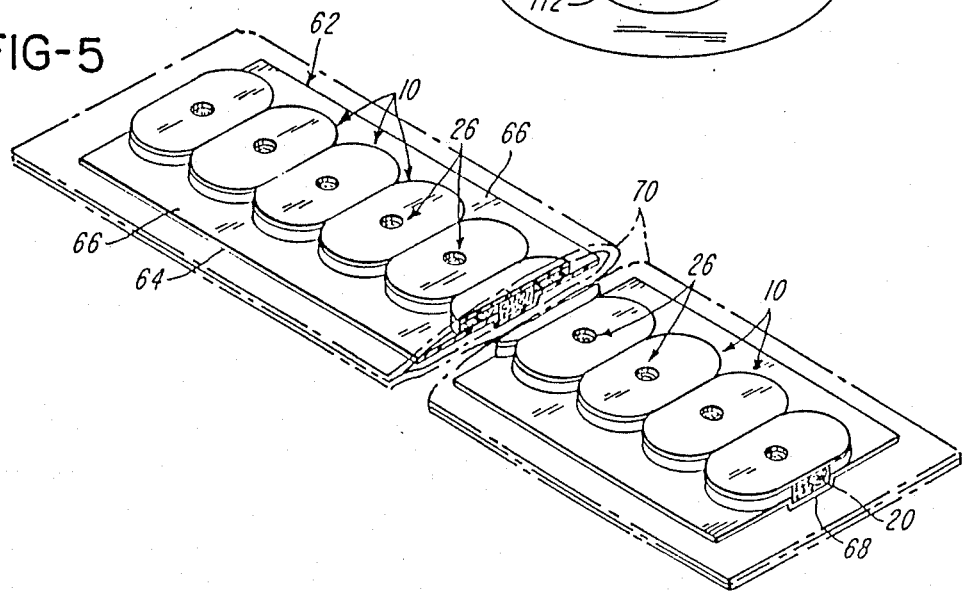

MEDICAL ELECTRODE WITH REUSABLE CONDUCTOR AND METHOD OF MANUFACTURE

This is a divisional of co-pending application Ser. No. 756,752, filed on July 18, 1985, now U.S. Pat. No, 4,635,642, granted Jan. 13, 1987.

This is a continuation of co-pending application Ser. No. 920,028 now abandoned filed on Oct. 16, 1986.

SUMMARY OF THE INVENTION

The present invention relates to a medical electrode for transmitting electrical signals between the skin of a subject, such as a medical patient, and peripheral equipment for monitoring signals derived from the skin of the patient. This invention may, however, also be used for medical electrodes for applying stimulation signals to the skin of the patient.

There is a continuing need for high quality but inexpensive medical electrodes. This is especially true for test procedures, such as ECG's, done while the patient is at rest, wherein several electrodes, usually ten, twelve, or fourteen, are used at a time. Reliable traces representing the signals produced by a patient's heart are obviously important. Further, for purposes of convenience and safety, such electrodes should be so inexpensive that it is practical to dispose of them after only one use. Accordingly, a primary object of this invention is to provide an inexpensive, high quality medical electrode.

One approach to providing inexpensive medical electrodes has been to provide a disposable electrode pad including an electrolyte and a carrier therefor and a reusable electrode conductor which is attached to a cable used for connection to external monitoring equipment. It is generally recognized that, in order to obtain high quality traces, the portion of the electrode conductor engaged with the electrolyte should be a substantially pure metal, either substantially pure silver or a silver coated conductive plastic being preferred for ECG's taken with the patient at rest. Electrode conductors usually comprise the most expensive part of a medical electrode so that, by providing a reusable electrode conductor, substantial economies may be had because the more expensive conductor may be reused many times while the less expensive electrode pad is discarded after each use. This invention takes advantage of this approach and it is a further object of this invention to provide an improved high quality but inexpensive and disposable electrolyte pad comprising an electrolyte and a carrier therefor and a method of manufacturing the same.

One of the important considerations in the construction of an electrode of the type have a reusable conductor is the manner in which the conductor is attached to the electrode pad. In practice, several electrode pads are adhered to the skin of a patient and the electrode conductors are thereafter connected to the pads. Such connections, and subsequent disconnections, should be readily made without causing discomfort to the patient. Also, to obtain high quality traces, the connection should be sufficiently secure that the electrode conductor is held firmly engaged with the electrolyte. Therefore, it is a further object of the invention to provide a medical electrode of the type comprising a reusable conductor and a disposable electrode pad having an improved connection between the conductor and the electrode pad whereby the conductor can be easily and securely engaged with the electrolyte.

In accordance with this invention, a medical electrode is provided having an electrode pad comprising a laminated assembly of a pair of spaced, flexible, electrically non-conductive, foam sheets with patient-contacting adhesive layers on their lower surfaces. The gap between the foam sheets is filled with an electrolyte gel matrix, preferably a conductive adhesive, a urethane hydrogel being the material of choice, having a thickness greater than the foam sheets. The electrode pad further comprises an electrically non-conductive socket plate overlying the gel matrix and overlapping the foam sheets. The socket plate has an adhesive layer on its bottom surface adhered to the foam pads and the gel matrix and is provided with a socket for connection of the electrode conductor to external monitoring equipment. The socket preferably comprises a bore centrally located over the gel matrix and shaped to receive the electrode conductor. The electrode conductor is slightly larger than the bore, and the adjacent area of the socket plate resiliently holds the electrode conductor therein. In a modified form, the socket further includes radially extending slits projecting from the outer margins of the bore.

The electrode conductor is attached to a reusable lead wire having a jack for connection to external monitoring equipment. For connection to the lead wire, the electrode conductor may be provided with a snap fastener-type stud. In addition, the electrode conductor has a ridged body so constructed that the portions of the socket plate surrounding the bore resiliently engage the conductor between its ridges and thereby maintain the conductor in engagement with the electrolyte matrix. In a modification preferred for longer term monitoring uses, the socket and the electrode conductor are provided with a cooperating key and keyway for restraining relative movements therebetween.

For short term monitoring, a strip of electrode pads is mounted on an elongate release liner or a formed tray with adjacent electrodes abutting one another. For economy of manufacture, the foam sheets initially comprise adhesively coated webs or strips of indefinite length laid along the opposite margins of the release liner or formed tray and the gel matrix is deposited as a continuous strip on the release liner between the foam strips. The socket plates for the electrode pad strip are formed from a web of relatively stiff, adhesively coated, plastic sheet material from which the sockets have been die cut and which is laid over the foam strips and the deposited gel matrix. The parts thus assembled are then die cut to shape and to separate the individual electrodes and to sever the parts into separate electrode pad strips. Electrode pads formed in the manner have their electrolyte exposed both through the sockets and along their sides. To prevent drying out of the electrolyte during shipment and storage, the individual strip of electrode pads is preferably packaged in an air tight envelope or the like. During a short term monitoring procedure, electrolyte dry out is not a matter of concern. Therefore, the fact that the gel matrix is exposed along the side edges of an electrode pad does not detract from the utility of the electrode. For longer term monitoring applications, each electrode pad is preferably constructed so that, when applied to the skin of a patient, its gel matrix is confined so as to avoid dry out.

Other objects and advantages of this invention will become apparent from the following description and the drawings.

BRIEF DESCRIPTION OF THE DRAWINGS

FIG. 1 is a perspective view of a single medical electrode pad of this invention, a lead wire therefor, portions of which have been broken away, and an electrode conductor.

FIG. 2 is an enlarged, fragmentary, cross-sectional view of the medical electrode pad, the lead wire, and the electrode conductor taken generally on line 2—2 of FIG. 1.

FIG. 3 is a fragmentary, cross-sectional view, on the same scale as FIG. 2, of a portion of the electrode pad of FIG. 1 and showing the electrode conductor operatively connected thereto.

FIG. 4 is a perspective view schematically illustrating steps taken in the preferred method of manufacturing a plurality of medical electrode pads in a strip in accordance with this invention.

FIG. 5 is a perspective view, with parts broken away, of a completed electrode pad strip in accordance with the invention and showing, by phantom lines, an air tight package for the strip.

FIG. 6 is a perspective view of a modified medical electrode pad in accordance with this invention.

FIG. 7 is a plan view of a second modified medical electrode pad in accordance with this invention.

FIG. 8 is an exploded perspective view of the electrode pad of FIG. 7 and a lead wire provided with a modified electrode conductor in accordance with this invention.

DESCRIPTION OF THE PREFERRED EMBODIMENTS

With reference to FIGS. 1, 2 and 3, a medical electrode according to the present invention includes a disposable electrolyte carrier or electrode pad generally designated 10 which comprises a laminated assembly of a pair of spaced, parallel, flexible, sheets of foam plastic, designated 12 and 14, respectively, having adhesive layers 16 and 18, respectively, on their lower surfaces. The sheets 12 and 14 are made from electrically nonconductive foam material and may comprise any of a wide variety of closed cell thermoplastic foams which are well known in the art, the material of choice for the present invention being a polyethylene foam. Adhesive layers 16 and 18 may comprise any conventional electrically non-conductive pressure sensitive adhesive of the type generally known as "patient contact" adhesives which may be safely used to affix the electrode pad 10 to the skin of a patient.

The gap between the foam sheets 12 and 14 is filled with a matrix 20 of electrolyte gel, the gel matrix 20 preferably comprising a conductive adhesive and having a thickness greater than the foam sheets 12 and 14. Various conductive materials may be used depending upon the application for which the electrode is intended. The material of choice for the present application is a urethane hydrogel which is of a gelatinous consistency and which contains an electrolyte in an amount sufficient to render it electrically conductive. The electrolyte comprises an ionizable salt compatible with the metal used to form the electrode conductor which will be described below. These are well known in the art; examples are the use of sodium chloride when the conductor is made from or coated with silver, as is presently preferred, and the use of sodium sulfate with stainless steel.

Alternate materials that may be used for the electrolyte include a commercially available conductive adhesive composition comprising karaya gum modified with sodium chloride, available from LecTec Corporation, 120 South Crosstown Circle, Eden Prairie, Minn. Various other conductive adhesive compositions that may be usable are described in the following U.S. Pat. Nos.: Marks et al. 3,357,930; Kater 3,993,049; Berg 4,066,078; Hymes 4,125,110; Cross et al. 4,141,366; and Hymes 4,274,420. Whatever the composition of the conductive adhesive, it should be of the type which will adhere to the skin of a patient and will have a cohesive strength sufficient to substantially maintain its shape and to permit it to be peeled from the skin to which is it attached without leaving any appreciable residue.

Overlying the gel matrix 20 and overlapping the foam sheets 12 and 14 is a socket plate 22 that has an electrically non-conductive, pressure-sensitive, adhesive layer 24 on its bottom surface by which it is adhered to the foam sheets 12 and 14 and the gel matrix 20. Socket plate 22 and its underlying adhesive 24 perform the functions of maintaining the shape of the electrode pad 10, of providing a covering for the gel matrix 20, and of providing a socket 26, in the form of a centrally located, circular bore, extending through the socket plate 22, for connection of the electrode pad 10 to external monitoring equipment. The socket plate 22 comprises a relatively stiff sheet of electrically non-conductive thermoplastic material such as styrene, vinyl, or polyethylene terephthalate (Mylar). In general, the socket plate 22 should be resiliently flexible but sufficiently stiff that it will firmly hold the electrode conductor within the socket 26 as will be described below. Mylar sheet having a thickness of approximately 4 or 5 mils or vinyl sheet of approximately 5 or 6 mils are examples of materials from which the socket plate 22 could be made.

Further, in accordance with this invention, a reusable lead wire, generally designated 32 having a jack 34 for electrical connection of the electrode pad 10 to external monitoring equipment is provided with an electrode conductor 36 adapted to extend through and be retained by the socket 26 so that it is lodged in the gel matrix 20 as shown in FIG. 3. Except for the provision of the electrode conductor 36, the lead wire 32 may be of the type conventionally used to connect external equipment to medical electrodes having snap fastener studs, and includes a jacketed cable 38 connected to a lead wire connector 40, which is shaped as a female snap fastener socket, by wiring 42 inside a molded head member 44. An insulating plastic sleeve 46 covers the area where the exposed cable is crimped to the jack 34.

With reference to FIGS. 2 and 3, the electrode conductor 36 preferably comprises a one-piece, generally cylindrical conductive body having a snap fastener-type stud 48 formed on and projecting upwardly from the top surface of its generally cylindrical body. Since, in the contemplated use of this invention, the electrode pad 10 will be discarded after each use but the lead wire 32 with its electrode conductor 36 will be repeatedly used with like electrode pads, it is intended that the electrode conductor 36 will be permanently assembled on the lead wire head member 44. Therefore, the stud 48 is preferably slightly larger than conventional studs with which the female socket 40 is designed for use so that the stud 48 will be so tightly held in the socket 40 that separation of the electrode conductor 36 from the lead wire head member 44 would be difficult. As an option, the electrode conductor 36 could be permanently connected to the remainder of the lead wire 32. Various ways of making such a permanent connection will be readily apparent.

For optimum transmission of signals, it is preferred that the electrode conductor 36 comprise substantially pure silver or be plated or coated with substantially pure silver and that its outer surface be chlorided. Since a low cost is important, the presently preferred electrode conductor comprises a conductive nylon, rendered conductive by inclusion of carbon, that preferably has a silver coating, which may be painted or plated, at least along a portion of its surface that engages the gel matrix 20. It would also be possible to use a silver plated non-conductive plastic, such as ABS, but it is believed that such an electrode conductor may have a sufficient portion of its silver plating removed by abrasion resulting from repeated applications to the electrode pads that the continuity of the silver plating may be lost so quickly that the useful life of the electrode conductor would be unsatisfactorily limited. Other metals could be used, such as stainless steel, but silver provides the highest quality traces.

The cylindrical body of the illustrated electrode conductor 36 has a concave bottom surface 50, a beveled lower outer wall 52 in the form of an inverted, truncated cone, sloping upwardly and outwardly from the bottom surface 50 that terminates at its upper end in a circular ridge or shoulder 54. Above the ridge or shoulder 54, there are plural additional circular ridges or shoulders 56 formed at the upper ends of each of plural body sections that also are in the form of inverted, truncated cones but which have a lesser height than the lower wall surface 52. Accordingly, the portion of the outer wall of the body of the electrode conductor 36 extending out of the head member 44 has plural, closely-spaced, parallel ridges or shoulders 54 and 56 separated by plural grooves, designated 58.

The ridges or shoulders 54 and 56 have a diameter sightly greater, on the order of 0.010 to 0.020 inch, than the diameter of the socket bore 26. As an example, an electrode pad having a socket bore diameter of approximately 0.344 inch may be used with an electrode conductor having an outermost ridge diameter of approximately 0.355 inch. When an electrode pad 10 of this invention is to be used, it is adhered to the skin of a patient utilizing primarily the adhesive layers 16 and 18 on the bottom surfaces of the foam sheets 12 and 14 and also utilizing the inherent tackiness of the gel matrix 20. The lead wire 32 is then connected to the electrode pad 10 by inserting the lower portion of the electrode conductor 36 through the bore 26 and into the area occupied by the gel matrix. As shown in FIG. 3, because the lowest ridge or shoulder 54 has a diameter greater than the bore 26, the beveled lower outer wall 52 of the electrode conductor 36 pushes the margins of the socket bore 26 downwardly as the electrode conductor 36 is inserted therein. This is feasible because the socket plate 22 is resiliently flexible and because the electrode conductor 36 is only minimally larger than the bore 26. Ultimately, the ridge 54 passes the bore 26 and, due to the resiliency of the socket plate 22, the margin of the bore 26 is biased to enter the groove 58 immediately above the lowest shoulder 54. As shown in FIG. 3, when the electrode conductor 36 passes through the bore 26, it becomes intimately engaged with the gel matrix 20. The bottom surface 50 of the electrode conductor 36 is made concave to provide a pocket for receiving the gel. Accordingly, the distance by which the gel matrix 20 is displaced downwardly upon connection of the lead wire 32 in the electrode pad 10 is minimized. Here it may be noted that FIG. 3 shows the electrode conductor 36 inserted into the bore 26 of the electrode pad 10, but the electrode pad 10 is not shown applied to the skin of a patient. In practice, such would ordinarily not be done. Also, it may be noted that, although the margins of the bore 26 are shown lodged in the groove 58 immediately above the lowest shoulder 54, the electrode conductor 36 could be inserted more deeply into the area of the gel matrix 20.

The lead wire 32 may also be provided with an insulating washer 60 for preventing the gel material from reaching the lead wire connector 40. The washer 60 could be integral with the electrode conductor 36 and there may be occasions, depending upon the construction of the lead wire head member 44 or the nature of the gel matrix, when it would not be needed.

Those familiar with the art will recognize that the electrode pad 10 would be mounted on a release liner or silicon coated formed tray covering the adhesive layers 16 and 18 and the lower surface of the gel matrix 20 from which the electrode pad 10 would be removed immediately prior to use.

The electrode pad 10 is intended primarily for use in short term applications, such as for ECGs accomplished while a patient is at rest. For such applications, it is common practice to use ten, twelve, or fourteen electrodes at a time. With reference to FIG. 5, it is preferred that an electrode strip 62 be formed from the desired number of electrode pads 10 and from a release liner 64 on which the electrode pads 10 are located in mutually abutting, side-by-side relation. The release liner 64 may comprise an elongate strip of silicon coated paper, styrene, or the like formed with planar upper surface portions 66 on which the foam pads 12 and 14 rest, and further formed with a recessed central portion forming an axially extending trough 68 filled by the gel matrix 20.

The electrode strip 62 is preferably packaged for shipment and storage in a substantially air and moisture vapor impervious package or envelope shown by phantom lines 70, which may, as conventional, be made from a plastic and metal foil laminate. It will be observed that the gel matrix 20, which is susceptible to drying-out, is exposed to ambient atmosphere at the ends of the electrode strip 62. This is acceptable provided the electrode strip 62 is retained in a substantially air and water vapor impervious package as described until shortly before use since drying out is thereby avoided.

A preferred method of manufacturing plural electrode strips 62 on a continuous basis is schematically illustrated in highly simplified form in FIG. 4. There it will be observed that two adhesively coated foam strips or webs 12' and 14' of indefinite length have been preassembled onto a pair of release liners 71 and are continuously fed to a foam laminating roller 72 and a cooperating stripper roller 74 that strips away the release liner 71. The rollers 72 and 74 may be rotatably driven in any suitable way. The laminates of the adhesively coated foam strips 12' and 14' on the release liner 72 are preferably previously formed and wound into coils (not shown) from which they are drawn to the rollers 72 and 74 as they rotate. A strip 64' of release liner material of indefinite length, which may be supported by rolls or the like (not shown), is coursed along a path extending beneath the foam laminating roller 72 so that the foam webs 12' and 14' are laid along the opposite top sides of the release liner strip 64' beside the trough 68. Thereafter, the release liner strip 64' passes beneath a funnel or other means 76 which deposits a strip of electrolyte material, designated 20', that forms the gel matrix 20 into the trough 68. The assembly then passes under a power drive socket sheet laminating roller 77 to which is fed an assembly comprising a release liner 78 and a web of adhesively coated, relatively stiff, plastic sheet material 22' that is used to form the socket plates 22 and their underlying adhesive layers 24, which web 22' is placed over the previously assembled release liner strip 64' and electrolyte material 20'. The release liner 78 and the adhesively coated web 22' are preferably preassembled and then die cut to form the socket bores 26 in equally spaced relation along the entire length thereof. This assembly is then wound into a coil (not shown) from which it is fed to the laminating roller 77. A stripper roller 79 cooperates with the laminating roller 77 to strip away the release liner 78. Here it may be noted that the web 22' could be narrower than the release liner strip 64' and does not necessarily have to completely cover the foam sheets 12 and 14 of a completed electrode pad 10. Some convenience in handling the laminate is achieved if the web 22' is the same width as the release liner strip 64' and such construction is preferred.

The laminate thus formed thereafter passes under a roller die 80 provided with cutting elements 82 that cut the laminate into the individual electrode pads 10 and may also cut away marginal sections 84 of the foam webs 12' and 14' and the sheet material 22' to form the desired outer shape of the electrode pads 10. Although shape is not a critical factor, each electrode 10 is preferably formed to the generally oval configuration illustrated, with straight sides and rounded ends, since electrodes of such shape are readily die cut from an elongate laminate strip with minimal wastage of material. The cutting elements 82 are sized and shaped to cut through the entire laminate except for the release liner strip 64'. An appropriate cutter (not shown) is used to cut through the entire laminate, including the release liner strip 64, to form successive electrode strips 66 of the proper length. Such cutter means could be formed on the roller die 80 or may be separate therefrom.

Preferably, the gel material 20' is deposited in the trough 68 in a free-flowing, liquid state and permitted to set to a gelatinous, shape-retaining, state in the trough 68. In such case, it may be necessary or desirable to form or place barriers 86 in spaced parts of the trough 68 to cooperate with the trough 68 and the foam strips 12' and 14' to confine the gel material 20' while it is setting from its liquid state to its gelatinous state. in FIG. 4, the barriers 86 are shown above the troughs 68. In practice, they would be inserted into the trough 68 in advance of the depositing means 76. The barriers could be made from thin plastic or the like and could either be left in the trough 68 or removed after the gel material has set sufficiently to retain its shape. As an option, the release liner could be formed with integral barriers.

FIG. 6 shows a modified electrode pad 10A which has the same general construction as the pad 10 of FIG. 1, and like reference numbers are used for like parts in FIG. 1 and FIG. 6. The only difference in FIG. 6 is that the socket 26A includes a circular bore 90 and four, equally spaced, radially extending slits 92 projection from the outer margin of the bore 90. Because of the slits 92, the arcuate portions of the socket plate 22A immediately adjacent the bore 90 are effectively formed to have four flaps, designated 94, which are effectively resiliently hinged to adjacent parts of the socket plate 22' and, accordingly, readily bend downwardly as the electrode conductor 35 is inserted into the bore 92.

FIGS. 7 and 8 show an electrode pad 100 and a lead wire 102 suitable for longer term monitoring, such as may be practiced when monitoring a patient for several days in a hospital. Electrode pad 100 comprises a ring shaped, foam plastic body 104 made from closed cell polyethylene foam or the line having a patient-contacting, pressure sensitive adhesive layer 106 on its underside for attachment to the skin of a patient. The body 104 has a central bore 108 which receives a portion of a gel matrix 110, which may be made from the same material as the gel matrix 20 of the first embodiment, that, before use, also extends into a pocket 112 formed in the center of a protective cover 114 engaged with the adhesive layer 106. The cover 114 performs essentially the same function and may be constructed of the same material as the release liner 22. The adhesive 106 is covered along a peripheral portion thereof by a suitably shaped finger tab 116 to facilitate removal of the foam plastic body 104 from the protective cover 114. The cover 114 has an embossed arrow 118 to indicate the position of the finger tab 116.

Centrally located over the foam body 104 is a circular socket plate 120 having an adhesive layer 122 on its lower surface attaching the socket plate 120 to the foam body 104 and the gel matrix 110. Socket plate 120, which may be made from the same stiff sheet material as the socket plate 22 of the first embodiment, is provided with a socket 124 comprising a centrally located bore 126 having a circular center portion and a radially extending keyway 128. Plural slits 130 project radially from the center axis of the socket plate 120. For emphasis, the widths of the slits 130 are exaggerated in FIGS. 7 and 8. In practice, these would have no appreciable widths. Generally speaking, the bore 126 and the slits 130 perform the same functions as the bore 90 and the slits 92 of FIG. 6 in that they cooperate with a ridged electrode conductor 132 affixed to the head of the lead wire 102 to retain the electrode conductor engaged with the gel matrix 110. As will now be apparent, the provision of the slits 130 in the embodiment of FIGS. 7 and 8 is optional.

Because the embodiment of FIGS. 7 and 8 is intended for long term monitoring, the electrode conductor 132 is provided with a key 134, which also is ridged, that engages in the keyway 128 to further restrain relative rotation between the electrode conductor 132 and the electrode pad 100. The electrode conductor 132 and its key 134 have sightly larger margins than the bore 126 and the keyway 128 of the socket 124 so that the electrode conductor is firmly retained by the socket 124.

It is contemplated that the electrode pad 100 would also be stored in a plastic and metal foil wrapper during shipment and storage. Also, it may optionally be provided with a cover sheet (not shown) for covering the socket 124 to better protect the gel matrix 110 from drying out. When applied to the skin of a patient, the gel matrix 100 is confined to the skin, the surrounding foam body 104, the socket plate 120, and the electrode conductor. Accordingly, the electrode pad 100 may be used for substantially longer periods of time than the pad 10 of the first embodiment.

Although the presently preferred embodiment of this invention has been described, it will be understood that various changes may be made within the scope of the appended claims.

Having thus described our invention, we claim:

1. A disposable medical electrode pad of the type adapted to be removed from a release liner and applied to the skin of a patient for use with a reusable electrode conductor comprising a pair of mutually-spaced foam sheets having mutually substantially coplanar respective upper and lower surfaces, a patient-contacting adhesive on said lower surfaces, and a gap between mutually confronting edges of said sheets, an electrolyte gel matrix filling said gap, a socket plate overlying said gel matrix and overlapping said foam sheets, a said socket plate comprising a sheet of plastic and socket means overlying said gel matrix for removably assembling an electrode conductor in engagement with said gel matrix, and means adhering said socket plate to said foam sheets.

2. The pad of claim 1, wherein said electrolyte gel matrix comprises a hydrogel.

3. The pad of claim 1, wherein said electrolyte gel matrix comprises a urethane hydrogel.

4. For use with a reusable electrode conductor, the combination of a release liner and a disposable medical electrode pad comprising a pair of mutually-spaced foam sheets on said release liner, said pair of foam sheets having mutually confronting edges with a gap therebetween, an electrolyte gel matrix on said release liner filling said gap between said foam sheets, a socket plate overlying said gel matrix and overlapping said foam sheets, said socket plate comprising a sheet of plastic having a socket therein overlying said gel matrix for receiving an electrode conductor, said socket comprising a bore extending through said socket plate, and means adhering said socket plate to said foam sheets.

5. The combination of claim 4 wherein each of the sheets of said pair of foam sheets has a patient-contacting adhesive on its surface engaged with said release liner.

6. The combination of claim 4 wherein said release liner has a trough bounded by mutually-spaced surface portions on which each of the sheets of said pair of foam sheets are respectively located and said gel matrix fills said trough and the area between said foam sheets.

7. The combination of claim 6 wherein each of said foam sheets has a patient-contacting adhesive on its surface engaged with said release liner.

8. The combination of claim 4 wherein said electrolyte gel matrix comprises a hydrogel.

9. The combination of claim 4 wherein said electrolyte gel matrix comprises a urethane hydrogel.

10. For use with a reusable electrode conductor, a disposable medical electrode pad comprising a socket plate comprising a substantially flat sheet of relatively stiff plastic having first and second oppositely facing sides and socket means for receiving an electrode conductor, a pair of mutually-spaced foam sheets overlapped by said socket plate and extending from said first side to said second side of said socket plate, an electrolyte gel matrix between said foam sheets and underlying said socket plate and said socket, and means adhering said socket plate to one surface of each of said foam sheets, said foam sheets and said gel matrix each having exposed first edges extending below said socket plate on said first side of said of socket plate and exposed second edges extending below said socket plate on said second side of said socket plate, and each of said foam sheets having a patient-contacting adhesive on its surface opposite said one surface thereof adhered to said socket plate.

11. The pad of claim 10 wherein said electrolyte gel matrix comprises a hydrogel.

12. The pad of claim 10 wherein said electrolyte gel matrix comprises a urethane hydrogel.

13. The electrode of claim 10 wherein gel matrix is thicker than said foam sheets.

14. The pad of claim 13 wherein said electrolyte gel matrix comprises a hydrogel.

15. The pad of claim 13 wherein said electrolyte gel matrix comprises a urethane hydrogel.

16. For use with a reusable electrode conductor, an electrode assembly comprising a disposable medical electrode pad comprising an electrolyte gel matrix and a socket plate overlying said gel matrix, said socket plate comprising a sheet of plastic having a socket therein overlying said gel matrix for receiving an electrode conductor, said socket comprising a bore extending through said socket plate and a plurality of slits extending outwardly from said bore so that said socket plate has flaps adjacent said bore, each bounded by a pair of said slits, said flaps defining means aiding in the retention of said electrode conductor.

17. The electrode assembly of claim 16 further comprising a release liner, a pair of mutually-spaced foam sheets on said release liner, said gel matrix being on said release liner between said foam sheets, and means adhering said socket plate to said foam sheets.

18. The electrode assembly of claim 17 wherein said foam sheets have a patient-contacting adhesive on their surfaces engaged with said release liner.

19. The electrode assembly of claim 17 wherein said release liner has a trough bounded by surface portions on which said foam sheets are located and said gel matrix fills said trough and the area between said foam sheets.

20. The electrode assembly of claim 16 further comprising a release liner, a foam body having an adhesive coating on its bottom surface engaging said release liner, said foam body having a bore extending therethrough, and said gel matrix being positioned on said release liner and within said last mentioned bore.

21. The electrode assembly of claim 16 wherein said socket further includes a keyway adapted to interfit with a reusable electrode conductor having a key adapted to fit within said keyway to restrain relative movement between said pad and said conductor.

22. For use with reusable electrode conductors, a strip assembly comprising:
   a release liner comprising an elongate strip of sheet material formed with a central, longitudinally-extending trough bounded by mutually-spaced, upwardly-facing surface portions of said liner; and
   a plurality of disposable medical electrode pads aligned in side-by-side relationship on said release liner, each of said pads comprising:
      a pair of mutually-spaced foam sheets each located respectively on one of said upwardly facing surface portions of said release liner, an electrolyte gel matrix filling the entire length of said trough bounded by said foam sheets and the area between said foam sheets, and a socket plate adhered to said foam sheets and overlying said gel matrix, said socket plate comprising a sheet of plastic having a socket therein overlying said gel matrix for receiving an electrode conductor, said socket comprising a bore extending through said socket plate.

23. The strip assembly of claim 22 wherein said foam sheets have a patient-contacting adhesive on their surfaces engaged with said release liner.

24. The strip assembly of claim 22 wherein said socket of each of said pads further comprises a plurality of slits extending outwardly from said bore so that said socket plate has flaps adjacent said bore, each bounded by a pair of said slits, said flaps defining means aiding in the retention of said electrode conductor.

25. The strip assembly of claim 22 wherein said socket of each of said pads further includes a keyway adapted to interfit with a reusable electrode conductor having a key adapted to fit within said keyway to restrain relative movement between said pad and said conductor.

26. The strip assembly of claim 22 wherein said foam sheets have a patient-contacting adhesive on their surfaces engaged with said release liner.

27. The strip assembly of claim 22 wherein said electrolyte gel matrix comprises a hydrogel.

28. The strip assembly of claim 22 wherein said electrolyte gel matrix comprises a urethane hydrogel.

29. For use with reusable electrode conductors, a strip assembly comprising:
a release liner comprising an elongate strip of sheet material formed with a longitudinally-extending center portion bounded by mutually-spaced, longitudinally-extending, upwardly-facing surface portions of said liner; and a plurality of disposable medical electrode pads aligned in side-by-side relationship on said release liner, each of said pads comprising:
a pair of mutually-spaced foam sheets each located respectively on one of said upwardly facing surface portions of said release liner, each of said foam sheets having a patient-contacting adhesive on their surfaces engaged with said release liner, an electrolyte gel matrix filling the area between said foam sheets and a socket plate adhered to said foam sheets and overlying said gel matrix, said socket plate comprising a sheet of plastic and socket means overlying said gel matrix for removably assembling an electrode conductor in engagement with said gel matrix.

30. The strip assembly of claim 29 wherein said electrolyte gel matrix comprises a hydrogel.

31. The strip assembly of claim 29 wherein said electrolyte gel matrix comprises a urethane hydrogel.

32. The strip assembly of claim 29 wherein said upwardly facing surfaces portions are mutually substantially coplanar and said central portion of said release liner comprises gel matrix-receiving means beneath the plane of said upwardly facing surface portions for enabling parts of said gel matrix to extend below the level of the said foam sheets in addition to filling the area between them.

33. The strip assembly of claim 32 wherein said electrolyte gel matrix comprises a hydrogel.

34. The strip assembly of claim 32 wherein said electrolyte gel matrix comprises a urethane hydrogel.

* * * * *

UNITED STATES PATENT AND TRADEMARK OFFICE
CERTIFICATE OF CORRECTION

PATENT NO. : 4,827,939
DATED : May 9, 1989
INVENTOR(S) : James V. Cartmell, Larry R. Burcham, Michael L. Wolf It is certified that error appears in the above-identified patent and that said Letters Patent is hereby corrected as shown below:

On the title page, in item [60] Related U.S. Application data, "Ser. No 956,752" should read --Ser. No. 756,752--; in the references cited, "3,362,633 1/1967" should be --3,862,633 1/1975--. Column 1, line 55, "have" should be --having--; column 1, line 65, "the" should be --this--. Column 2, line 56, "the" should be --this--. Column 4, line 27, "bore," should be --bore--. Column 6, line 63, "liner 72" should be --liner 71--. Column 7, line 7, "The" should be --This--; column 7, line 43, "strip 64" should be --strip 64'--; column 7, line 53, "in" should be --In--. Column 8, line 5, "conductor 35" should be --conductor 36--; column 8, line 11, "line" should be --like--; column 8, line 62, "to" should be --by--. Claim 10, line 14, (column 9, line 65), "of said of" should be --of said--.

Signed and Sealed this

Nineteenth Day of February, 1991

*Attest:*

HARRY F. MANBECK, JR.

*Attesting Officer*      *Commissioner of Patents and Trademarks*